(12) United States Patent
Sailer et al.

(10) Patent No.: US 11,443,854 B2
(45) Date of Patent: Sep. 13, 2022

(54) IDENTIFYING POTENTIAL MEDICINAL INTERACTIONS FOR ONLINE CLINICAL TRIAL STUDY GROUPS

(71) Applicant: International Business Machines Corporation, Armonk, NY (US)

(72) Inventors: Anca Sailer, Scarsdale, NY (US); Kevin Paul Julier, Ridgefield, CT (US); Ajay Mohindra, Yorktown Heights, NY (US); Mujeebur Rahman, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 60 days.

(21) Appl. No.: 16/799,249

(22) Filed: Feb. 24, 2020

(65) Prior Publication Data
US 2021/0265062 A1    Aug. 26, 2021

(51) Int. Cl.
*G16H 50/70*     (2018.01)
*G06F 16/9536*   (2019.01)
(Continued)

(52) U.S. Cl.
CPC ........... *G16H 50/70* (2018.01); *A61B 5/4848* (2013.01); *G06F 16/9536* (2019.01);
(Continued)

(58) Field of Classification Search
CPC ........ G16H 50/70; G16H 10/60; G16H 70/40; G16H 15/00; G16H 20/90; G16H 10/20;
(Continued)

(56) References Cited

U.S. PATENT DOCUMENTS

| 8,019,623 B2 | 9/2011 | McCallie et al. |
| 10,262,107 B1 * | 4/2019 | Tran ................... G06F 19/3475 |

(Continued)

FOREIGN PATENT DOCUMENTS

| CN | 101676717 A | 3/2010 |
| CN | 102682162 A | 9/2012 |
| CN | 102879486 A | 1/2013 |

OTHER PUBLICATIONS

C. Sun, et al., "Chimera: Large-Scale Classification using Machine Learning, Rules, and Crowdsourcing", 40th International Conference on Very Large Data Bases, Sep. 1-5, 2014, Hangzhou, China, Proceedings of the VLDB Endowment, vol. 7, No. 13, http://pages.cs.wisc.edu/~anhai/papers/chimera-vldb14.pdf, 12 pages.

(Continued)

*Primary Examiner* — Robert A Sorey
*Assistant Examiner* — Kimberly A. Sass
(74) *Attorney, Agent, or Firm* — Edell, Shapiro & Finnan, LLC (57) ABSTRACT

Techniques are provided for identifying interactions between natural medicines and modern medicines. A corpus of information is analyzed pertaining to interactions of natural medicines with modern medicines for treating a condition. A mapping is created, wherein natural medicines are mapped to modern medicines for treating the condition. An on-line clinical trial study group is created, allowing participation by users, wherein a participation in a group is (Continued)

allowed for a selected set of users based on a group medication usage profile. Information from participants in each group is collected, and the collected information is analyzed.

16 Claims, 7 Drawing Sheets

(51) Int. Cl.
*G16H 20/10* (2018.01)
*G16H 10/20* (2018.01)
*A61B 5/00* (2006.01)
*G16H 15/00* (2018.01)
*G16H 70/40* (2018.01)
*G06Q 50/00* (2012.01)
*G16H 20/90* (2018.01)
*G16H 10/60* (2018.01)

(52) U.S. Cl.
CPC .............. *G06Q 50/01* (2013.01); *G16H 10/20* (2018.01); *G16H 10/60* (2018.01); *G16H 15/00* (2018.01); *G16H 20/10* (2018.01); *G16H 20/90* (2018.01); *G16H 70/40* (2018.01)

(58) Field of Classification Search
CPC .... G16H 20/10; G06Q 50/01; G06F 16/9536; A61B 5/4848
See application file for complete search history.

(56) References Cited

U.S. PATENT DOCUMENTS

| | | | |
|---|---|---|---|
| 2011/0153361 A1* | 6/2011 | Hanina | G16H 20/00 705/3 |
| 2015/0006190 A9* | 1/2015 | Glauser | G16H 20/10 705/2 |
| 2016/0048655 A1* | 2/2016 | Maitra | G16H 20/10 705/3 |
| 2017/0154166 A1* | 6/2017 | Klein | G16H 40/20 |
| 2017/0293738 A1 | 10/2017 | Bender et al. | |
| 2018/0166175 A1 | 6/2018 | Shah et al. | |
| 2019/0051396 A1 | 2/2019 | Hasegawa | |
| 2020/0020423 A1* | 1/2020 | Wu | G16H 10/60 |

OTHER PUBLICATIONS

S. Schnitzer, et al., "From Task Classification Towards Similarity Measures for Recommendation in Crowdsourcing Systems", https://arxiv.org/pdf/1707.06562.pdf, arXiv:1707.06562v1 [cs.IR] Jul. 20, 2017, 3 pages.

* cited by examiner

NATURAL MEDICINE — STANDARD NAME/ALTERNATE NAMES — REPORTED SIDE EFFECTS

MODERN MEDICINE — STANDARD NAME/ALTERNATE NAMES — REPORTED SIDE EFFECTS — INDIVIDUAL ATTRIBUTES

IDENTIFYING POTENTIAL MEDICINAL INTERACTIONS FOR ONLINE CLINICAL TRIAL STUDY GROUPS

BACKGROUND

1. Technical Field

Present invention embodiments relate to determining interactions between medicines and generating groups for online clinical trial study groups.

2. Discussion of the Related Art

Many traditional, homeopathic, and alternative medicines (including dietary supplements), referred to as natural medicines, are now widely available. Some natural medicines have been used for hundreds or even thousands of years and are considered to be safe by practitioners of natural medicine. However, with the advent of modern medicine, which includes medicines that are manufactured or synthesized by pharmaceutical companies and are subject to regulatory review, it is possible that adverse interactions between these two categories of medicines may occur. These interactions may not be well-documented or even known.

Natural medicines may not be well-studied in large populations in combination with modern medicines, and limited information may be available regarding the effects of administering natural medicines together with modern medicines.

SUMMARY

According to embodiments of the present invention, methods, systems, and computer readable media are provided for identifying interactions between natural medicines and modern medicines. A corpus of information is analyzed pertaining to interactions of natural medicines with modern medicines for treating a condition. A mapping is created, wherein natural medicines are mapped to modern medicines for treating the condition. An on-line clinical trial study group is created, allowing participation by users, wherein a participation in a group is allowed for a selected set of users based on a group medication usage profile. Information from participants in each group is collected, and the collected information is analyzed.

In another aspect, a summary of the collected information is provided, wherein effects are ranked by frequency. This feature allows the most commonly occurring effects to be identified in a population of individuals.

In another aspect, the online clinical trial study group is established in an online forum in an automated manner. This allows clinical trial study groups to be set up and configured in an efficient manner.

In another aspect, the corpus includes an online forum, a private database, a public database and/or a social media forum. Present techniques may utilize information from any suitable source, in a wide variety of structures and formats.

In another aspect, collected information includes adverse effects, beneficial effects, medicine profiles of the users, and demographic information of the users. Present approaches may involve both adverse effects and synergistic effects, in specific populations of individuals having particular demographic characteristics. This offers the ability to identify effects in specific populations of individuals with specific characteristics.

In another aspect, natural medicine includes homeopathic and herbal remedies and modern medicine includes synthetic medicines. Natural medicines may not be well studied, and present techniques provide an approach to identify effects from taking natural medications in combination with modern medicines.

In another aspect, present techniques determine whether an effect between a modern medicine and a natural medicine is statistically significant among users in a clinical trial study group. In another aspect, present techniques determine which combinations of natural medicine and modern medicine of a plurality of medicines consumed by users are statistically correlated with an effect. Accordingly, by obtaining this information in an online format, having specific fields and structures, statistical analysis may readily be employed to determine whether an effect is statistically significant.

In another aspect, mapping comprises generating an ontology comprising natural medicines, modern medicines, and demographics of users. This structure streamlines the analysis process, as the ontology links medicines based on reported side effects.

It is to be understood that the Summary is not intended to identify key or essential features of embodiments of the present disclosure, nor is it intended to be used to limit the scope of the present disclosure. Other features of the present disclosure will become easily comprehensible through the description below.

BRIEF DESCRIPTION OF THE DRAWINGS

Generally, like reference numerals in the various figures are utilized to designate like components.

FIGS. 4A-4B are diagrams showing data components extracted from online information for identifying effects between natural medicines and modern medicines, according to an embodiment of the present invention. FIG. 4A shows categories of medicines. FIG. 4B shows examples of different reported side effects from combinations that overlap or are in common with an individual.

DETAILED DESCRIPTION

Online resources offer a wealth of information which may be analyzed to discover potential interactions between natural and modern medicines. Online resources, including social media and online forums, contain data which may be used to create a mapping of potential interactions between natural medicines and modern medicines. Once identified, online clinical trial study groups may be created to further elucidate and statistically validate such interactions.

Providers, patients, pharmaceutical companies, and regulatory agencies may be advised of potential side-effects and/or adverse reactions based on the information obtained from the online clinical trial study groups. In some cases, this information may be utilized to conduct actual clinical trials to study effects between traditional and modern medications.

Figure 1:
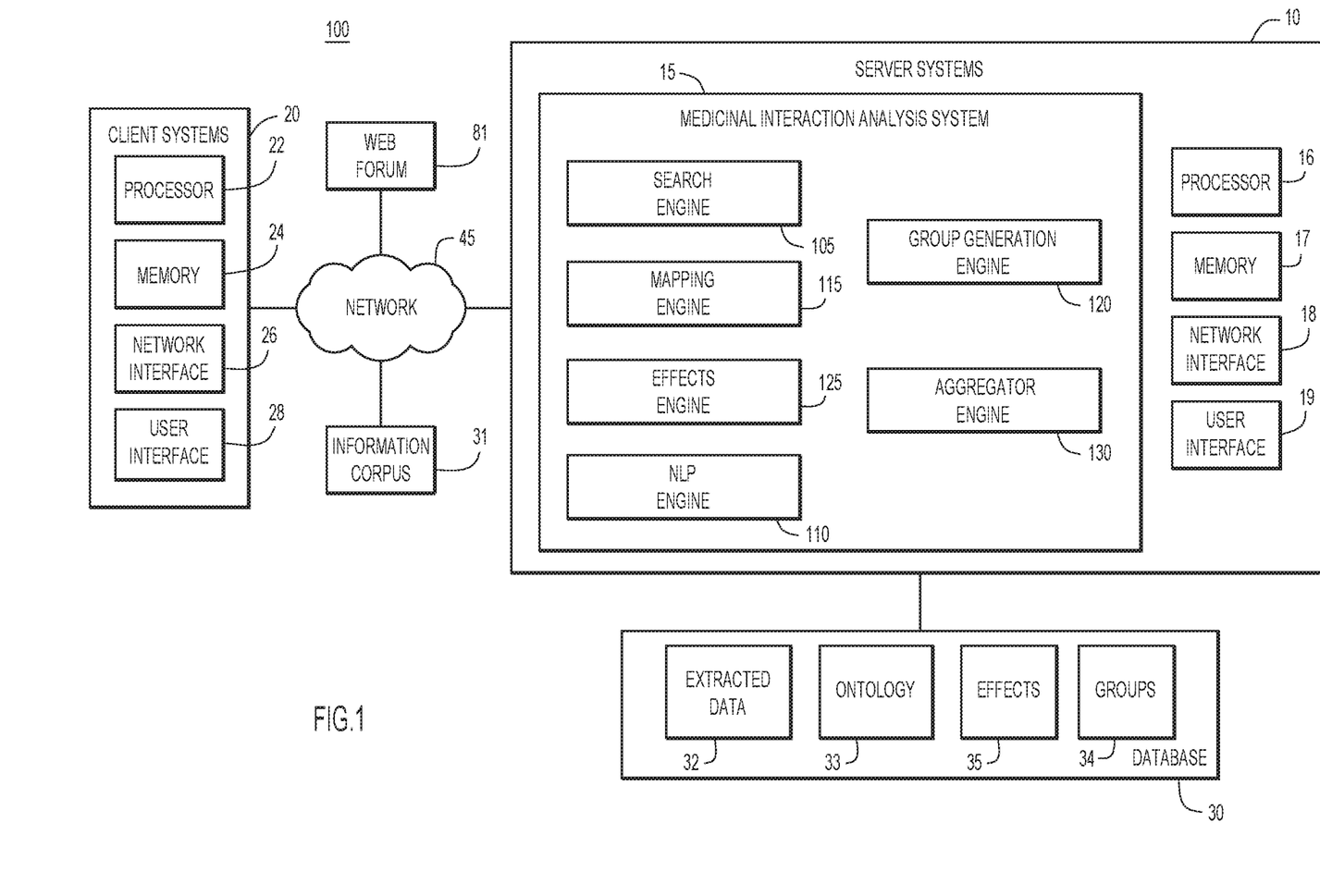
FIG. 1 is a diagrammatic illustration of an example computing environment for a medicinal interaction analysis system, according to an embodiment of the present invention.

An example environment for use with present invention embodiments is illustrated in FIG. 1. Specifically, the environment includes one or more server systems 10, one or more client or end-user systems 20, a database 30, and a network 45. Server systems 10 and client systems 20 may be remote from each other and may communicate over a network 45. The network may be implemented by any number of any suitable communications media, such as a wide area network (WAN), a local area network (LAN), Internet, Intranet, etc. Alternatively, server systems 10 and client systems 20 may be local to each other, and may communicate via any appropriate local communication medium, such as local area network (LAN), hardwire, wireless link, Intranet, etc.

Client systems 20 enable users to interact with various environments, performing activities which may generate queries that are provided to server systems 10. The server systems 10 include medicinal interaction analysis system 15, comprising a search engine 105, a natural language processing (NLP) engine 110, a mapping engine 115, a group generation engine 120 for generating online clinical trial groups, an effects engine 125, and an aggregator engine 130, as described herein.

A database 30 may store various information for the analysis, such as information obtained from the information corpus 31. Information corpus 31 may contain any relevant online resource containing information about natural and/or modern medicines. The medicinal interaction analysis system 15 may analyze an information corpus located in its native environment (e.g., online), or may generate and store a copy of the information corpus 31 locally in database 30 (not shown). The information corpus 31 may include any suitable information in a structured, semi-structured, or unstructured format, including but not limited to an online forum, a social media forum, a public database, a private database, literature references, or any other suitable repository. In some cases, information may be provided in a topic/response or question/answer format, in which responses or answers may be linked to a particular question or topic relating to a particular combination of medicines.

The information from the information corpus 31 may be processed by the medicinal interaction analysis system 15, and stored in database 30. For example, data from information corpus 31 may be processed and stored as extracted data 32, and converted into ontology 33. Ontology 33 may include information (e.g., extracted data 32) processed by NLP engine 110, and may include a mapping of natural to modern medicines with potential side effects. Online clinical trial study groups 34 may be established to further study suspected interactions/effects. Effects 35 may include additional information from clinical trial study groups 34 for potential interactions between natural and modern medicines.

Database 30 may store various information for the analysis, including extracted data 32, ontology 33, groups 34, and effects 35. The database system 30 may be implemented by any conventional or other database or storage unit, may be local to or remote from server systems 10 and client systems 20 and may communicate via any appropriate communication medium, such as local area network (LAN), wide area network (WAN), Internet, hardwire, wireless link, Intranet, etc. The system may establish online clinical trial groups to further study suspected interactions. The client systems may present a graphical user interface, such as a GUI, etc., or other interface, such as command line prompts, menu screens, etc., to solicit information from users regarding suspected interactions, and may provide reports or other information including whether information provided by the medicinal interaction analysis system 15 is successful in validating, e.g., statistically, potential interactions.

Server systems 10 and client systems 20 may be implemented by any conventional or other computer systems preferably equipped with a display or monitor, a base (including at least one hardware processor (e.g., microprocessor, controller, central processing unit (CPU), etc.), one or more memories and/or internal or external network interfaces or communications devices (e.g., modem, network cards, etc.), optional input devices (e.g., a keyboard, mouse or other input device), and any commercially available and custom software (e.g., server/communications software, medicinal interaction analysis system software, browser/interface software, etc.). By way of example, the server/client includes at least one processor 16, 22 one or more memories 17, 24 and/or internal or external network interfaces or communications devices 18, 26 such as a modem or network cards, and a user interface 19, 28 etc. The optional input devices may include a keyboard, mouse, or other input device. Client systems 20 may also be implemented by a mobile device such as a smartphone or tablet.

Alternatively, one or more client systems 20 may perform medicinal interaction analysis in a stand-alone mode of operation. For example, the client system may store or have access to the data, such as information corpus 31, and the stand-alone unit includes medicinal interaction analysis system 15. The system may establish online clinical trial groups to further study suspected interactions. The graphical user or other interface 19, 28, such as a GUI, command line prompts, menu screens, etc., solicits information from corresponding users regarding suspected interactions, and may provide reports or other information including whether information provided by the medicinal interaction analysis system 15 is successful in validating, at least statistically, potential interactions.

Medicinal interaction analysis system 15 may include one or more modules or units to perform the various functions of present invention embodiments described herein. The various modules (e.g., medicinal interaction analysis system 15, comprising a search engine 105, a NLP engine 110, a mapping engine 115, a group generation engine 120, an effects engine 125, and an aggregator engine 130, etc.), may be implemented by any combination of any quantity of software and/or hardware modules or units, and may reside within memory 17 of the server for execution by processor 16. These modules are described in additional detail below.

Search engine 105 crawls the information corpus 31 to identify relevant information. For example, search engine 105 may be configured to identify topics, threads, posts, or questions pertaining to interactions for medicines that an individual is consuming. Search engine 105 accesses this information, and provides this information to NLP engine 110 for analysis. For example, information may be extracted on a record by record basis or a thread by thread basis, or in any other suitable form. Some formats may retain the ability to link replies, answers, or information, to a particular topic, question, or subject.

NLP engine 110 relies on NLP techniques to extract relevant portions of information identified by search engine 105. This information may be in the form of semi-structured, structured or unstructured text. NLP engine 110 identifies content corresponding to medicine interactions as well as related information pertaining to medically relevant characteristics of individuals providing the data. In some aspects, NLP engine 110 may perform an analysis on a per-thread or per-question basis, extracting relevant content from each thread, and optionally linking this extracted information to a user identity, along with associated features that may be provided to other components of the medicinal interaction analysis system 15. Features may include author/user name, author/user medical history, author/user reported side effects, author/user medicines being consumed, etc.). The medicinal interaction analysis system 15 may process information via NLP engine 110 and store the results in database 30 as extracted data 32.

Mapping engine 115 may receive information from NLP engine 110 (e.g., extracted data 32) and may construct an ontology based upon this information. The ontology may link a modern medicine name to a natural medicine name, wherein links are formed based upon reported side effects. Additionally, the ontology may link to specific users, allowing medical characteristics of particular users to be linked to reported side effects. In some cases, user identity and medical characteristics from users may be anonymized, allowing the data to be analyzed without identifying the individual pertaining to the information.

Group generation engine 120 may analyze the ontology generated by mapping engine 115, and may create online clinical trial groups for further study of potential interactions between natural and modern medicines. The group generation engine may communicate with a web forum 81 to configure groups for the online clinical trial study and to set access policies, which allow access based upon medication usage profile. The system may invite users with medication usage profiles corresponding to an online clinical trial group to join the designated group. In some aspects, one or more of these operations may be automated.

In aspects, group generation engine 120 may generate a description of characteristics for a group for an online clinical trial study group (e.g., based on age, ethnicity, preexisting medical conditions, combinations of medicines taken, etc.). For example, group generation engine 120 may analyze user data, which may be anonymized, to identify characteristics of individuals reporting specific side effects. In some cases, side effects may be observed in individuals with pre-existing medical conditions, and may be influenced by age or other factors, etc. Accordingly, an online clinical trial group may be designed with particular demographic characteristics (e.g., with or without one or more preexisting conditions, etc.) to study effects in specific populations of individuals.

Effects engine 125 may analyze the information obtained from the web forum and ontology 33 to validate, at least statistically, effects from combinations of natural and modern medicines. For example, for the online clinical trial group, other individuals may provide information about natural and modern medicines being taken, and may report the same or different side effects. In some cases, a user may take the same combination of medicines as the originator and may report the same or different side effects or a combination thereof.

In other cases, an individual may be consuming a plurality of medicines, and the system may be configured to parse out side effects for subsets of medicines. For example, a user may be consuming three different types of medicines and may report corresponding side effects. Another user may report taking a subset of two medications reported by the originator without side effects, while yet another user may report taking a different subset of two medicines reported by the originator with similar side effects. In this case, the system may be able to identify a combination that causes side effects, while determining that other combinations do not have side effects. In aspects, the system may rank interactions based on particular medicine-medicine combinations, for groups of three or more medicines.

Based on this type of analysis, the effects engine 125 may link particular combinations of medicines to specific side effects in a population to identify which medicines of a plurality of medicines are linked to which side effects.

Aggregator engine 130 may utilize frequency information (e.g., frequency at which an effect from a combination of medicines is reported) to rank combinations of drugs that are likely associated with side effects in a population of individuals. In aspects, this information may be used to design and instigate actual clinical trials to study reported interactions.

Figure 2:
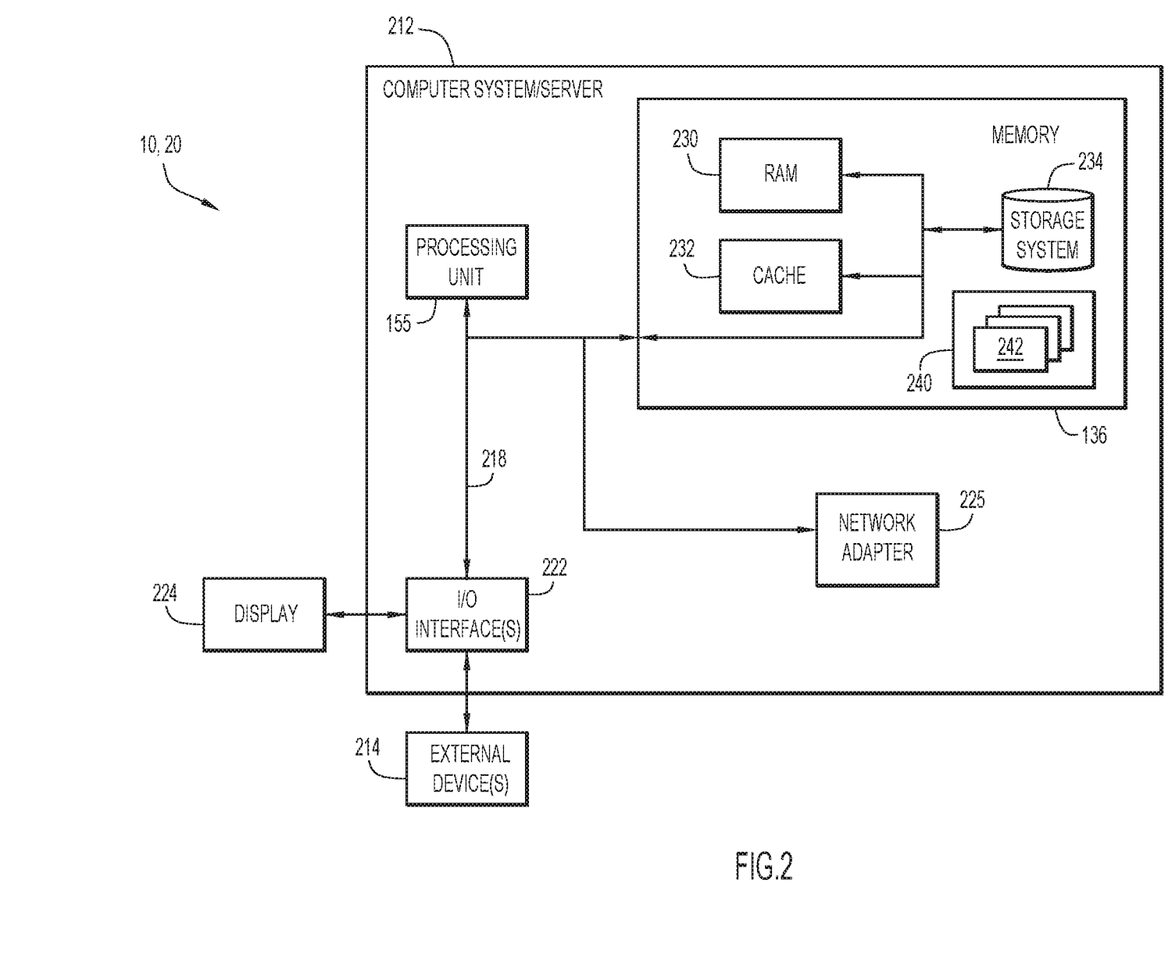
FIG. 2 is an example computing device for the computing environment of FIG. 1, according to an embodiment of the present invention.

Client systems 20 and server systems 10 may be implemented by any suitable computing device, such as computing device 212 shown in FIG. 2 for computing environment 100. This example is not intended to suggest any limitation as to the scope of use or functionality of embodiments of the invention described herein. Regardless, computing device 212 is capable of being implemented and/or performing any of the functionality set forth herein.

In the computing device, there is a computer system which is operational with numerous other general purpose or special purpose computing system environments or configurations. Examples of well-known computing systems, environments, and/or configurations that may be suitable for use with the computer system include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules (e.g., medicinal interaction analysis system 15 and its corresponding modules), being executed by a computer system. Generally, program modules may include routines, programs, objects, components, logic, data structures, and so on that perform particular tasks or implement particular abstract data types.

Computer system 212 is shown in the form of a general-purpose computing device. The components of computer system 212 may include, but are not limited to, one or more processors or processing units 155, a system memory 136, and a bus 218 that couples various system components including system memory 136 to processor 155.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and it includes both volatile and non-volatile media, removable and non-removable media.

System memory 136 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 136 may include at least one program product having a set (e.g., at least one) of program modules that are configured to carry out the functions of embodiments of the invention.

Program/utility 240, having a set (at least one) of program modules 242 (e.g., medicinal interaction analysis system 15 and corresponding modules, etc.) may be stored in memory 136 by way of example, and not limitation, as well as an operating system, one or more application programs, other program modules, and program data. Each of the operating system, one or more application programs, other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 225. As depicted, network adapter 225 communicates with the other components of computer system 212 via bus 218. It should be understood that although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
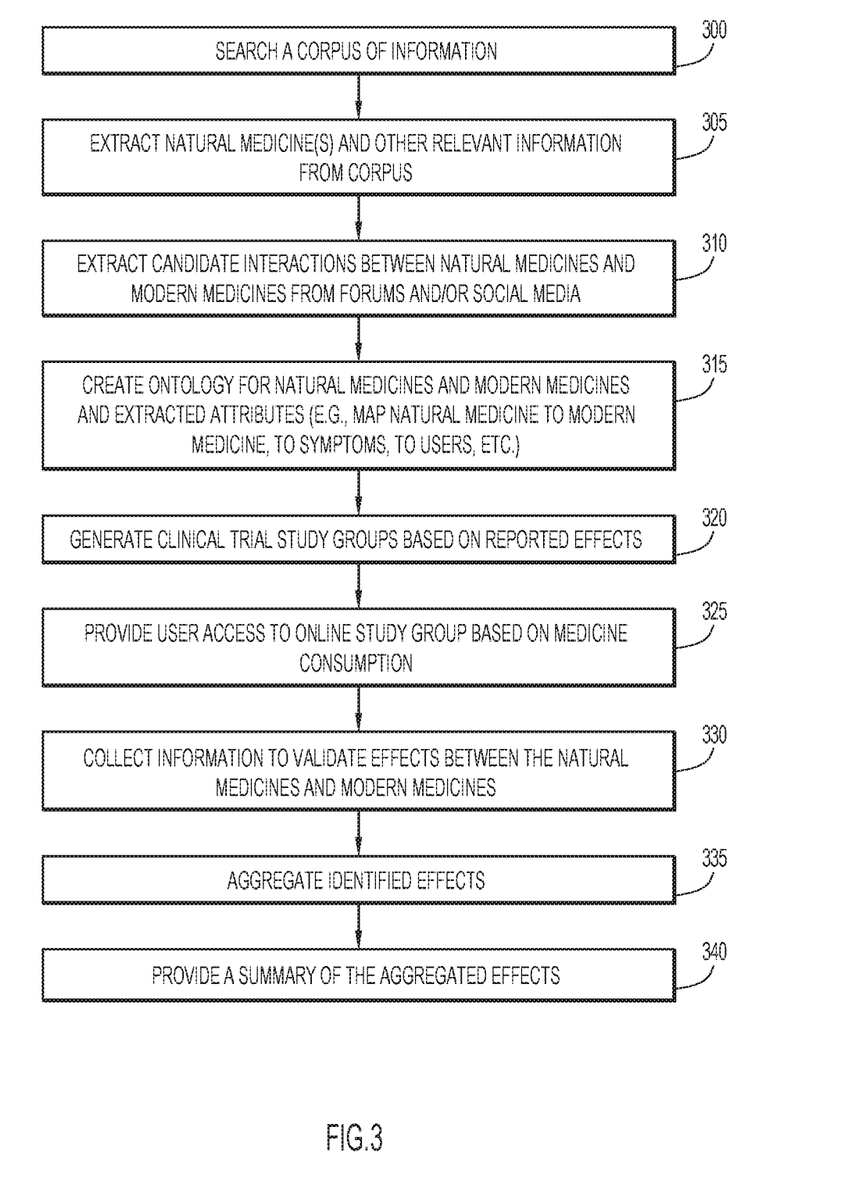
FIG. 3 is a flowchart showing operations for identifying effects between natural medicines and modern medicines using an online clinical trial study group, according to an embodiment of the present invention.

FIG. 3 is a flowchart showing example operations for determining natural and modern medicine interactions. At operation 300, a corpus of information is searched, e.g., by search engine 105, to obtain relevant information. This corpus may include databases involving adverse event reporting, literature resources involving natural medicines, or other structured, semi-structured, or partially structured information, including online forums and social media.

At operation 305, natural medicines and other relevant information pertaining to the natural medicines are extracted (e.g., by NLP engine 110) from the corpus. Natural medicines may include herbal remedies, teas, roots, homeopathic remedies, supplements, or other naturally occurring substances used for medicinal purposes. Extracted information may include common and alternative names for the natural medicine, as well as conditions for which the natural medicine may reportedly treat, as well as side effect of the medicine. Often, natural medicines have not been well-studied in a clinical trial and active ingredients may not be known. However, the origin of the natural medicine, for instance, the plant or other source from which the medicine is derived, may be known. This information may be used to derive potential side effects as well. In some cases, the system may filter side effects reported from consuming only the natural medicine or the modern medicine from side effects reported from consuming both the natural medicine and the modern medicine. Further, NLP engine 110 may identify specific conditions for which a natural medicine is being taken (e.g., cold, cough, fever, inflammatory conditions, immune response, etc.).

At operation 310, candidate interactions between natural medicines and modern medicines may be identified and extracted, also by NLP engine 110, from forums and social media sources. For example, an individual reportedly taking a specific combination of natural medicines and modern medicines may report experiencing specific side effects, such as an increase in blood pressure, a headache, nausea, dizziness, etc. The system may scan social information and online forums as well as adverse event databases to determine whether other interactions for this combination of medicines have been reported.

At operation 315, an ontology may be constructed by mapping engine 115, which maps natural medicines to modern medicines, based on a reported side effect. The ontology may include natural medicines, alternative names of natural medicines, modern medicines, alternative names of modern medicines, corresponding reported side effects, and user information and other attributes (as available). For example, user information may include demographic information, which is extracted and stored within the ontology. In some aspects, this information may be used to identify patient populations as part of an online clinical trial group, and may be extracted and stored in a manner to preserve patient anonymity.

Based on this information, at operation 320, online clinical trial study groups may be generated, based on reported effects. These groups may be used to further study whether a natural medicine and a modern medicine have an adverse effect or beneficial effect as reported in a larger population. At operation 325, the system may grant access to particular individuals to join particular study groups based on the specific natural and modern medicines that the individuals are consuming.

At operation 330, the system may collect additional data to validate effects as the study progresses. For example, the system may analyze the collected information, and determine whether reported side effects appear in a larger population at a frequency determined to provide statistical significance. Effects may include but are not limited to side effects, adverse effects, synergistic effects or improvements, etc.

At operation 335, effects may be aggregated. In some aspects, effects may be aggregated and ranked according to the most common effects reported. A summary of the aggregated results may be provided to the individual, as well as various personnel in the medical community, at operation 340.

Figure 4A:
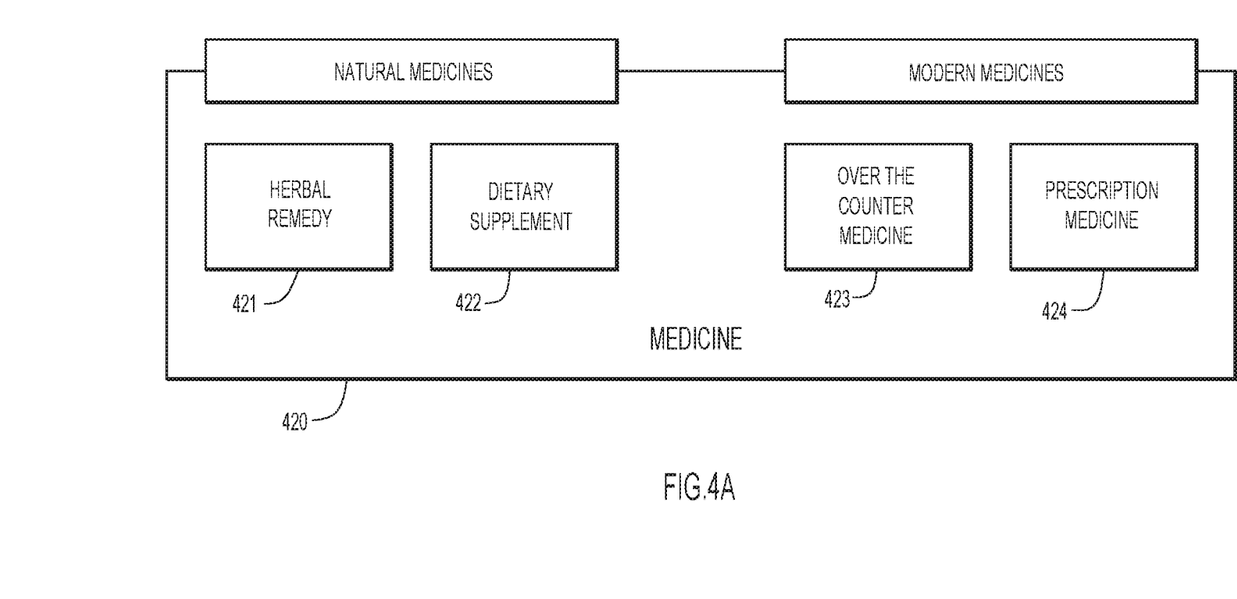
Figure 4B:
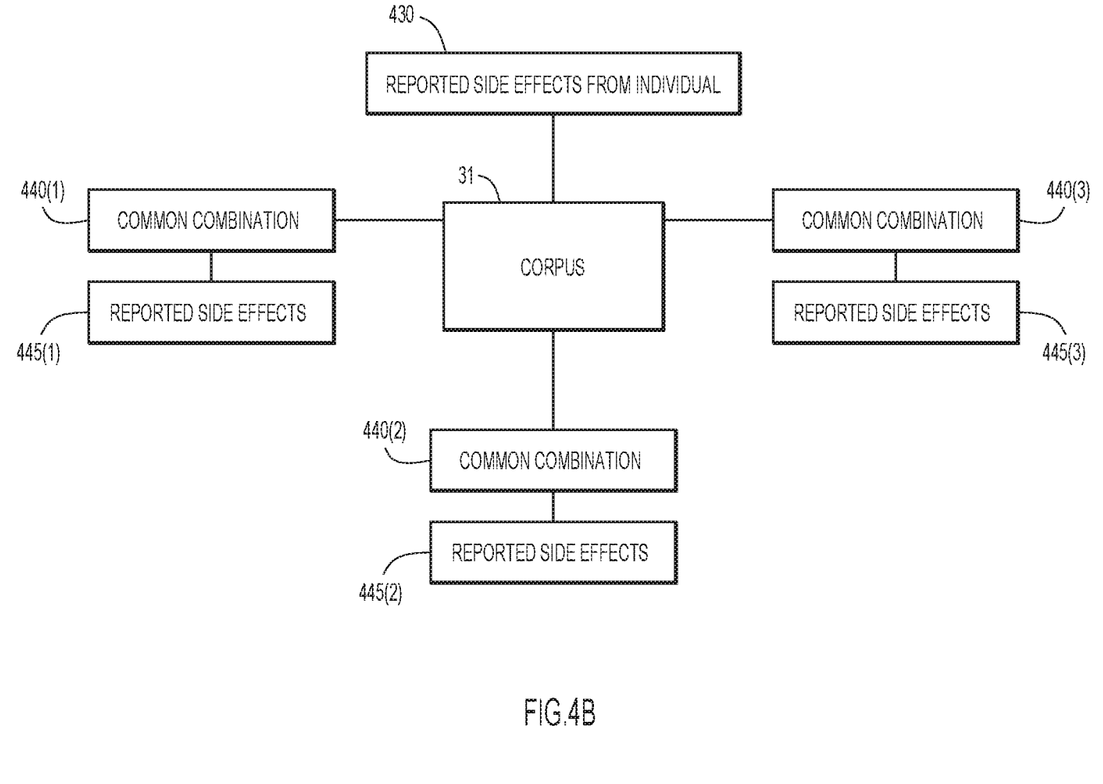

FIGS. 4A-4B show various data components according to embodiments of the present invention. Information obtained from a corpus of information (e.g., databases, online forums, social media, etc.) may be identified and extracted by NLP engine 110 as provided herein.

FIG. 4A shows categories of medicines. Medicine 420 may include different categories of medicine that an individual may take to alleviate or reduce physical symptoms of a medical condition. These include herbal remedy 421 which may include teas, herbs, roots, or other homeopathic remedies. Dietary supplements 422 may include vitamins, minerals, and other nutrients available for consumer purchase. Both herbal remedies and dietary supplements may be classified as natural medicines.

Over the counter medicines 423 include synthetic medicines for which a prescription is not required. Prescription medicines 424 include medicines for which a prescription is required. Typically, these categories have been studied in clinical trials and drug interaction information may be available, and are examples of modern medicines.

FIG. 4B shows examples of different reported side effects from combinations that overlap or are in common with individual 430. Reported side effects 430 from an individual taking a particular combination of medicines (in this example, at least three medicines) is shown. For example, corpus 31 may be analyzed to determine whether other individuals have taken this specific combination of drugs or a subset of these drugs. This is shown in common combinations 440(1) through 440(3). For each combination, reported side effects 445(1) through 445(3) are shown. For example, a first user may be taking the same combination as individual 430 (e.g., common combination 440(1)). Side effects for the user taking common combination 440(1) may be reported as reported side effects 445(1). A second user may be taking the same combination as individual 430 (e.g., common combination 440(2)) along with other medicines. A third user may be taking a subset of the medicines (e.g., common combination 440(3)) as individual 430. In some cases, the system may be able to identify drug combinations that are not associated with a side effect or may be able to identify subsets of medicine associated with a side effect.

This information may be extracted and used to generate an ontology including reported drug interactions, chemical structures, origin of the medicine (e.g., derived from a particular plant or other naturally occurring source), previously reported adverse events, individual demographics, etc. Once the ontology is created, clinical groups may be established to study the effects of combinations on a larger group of individuals and to identify drug-drug interactions in a complex drug space.

Figure 5:
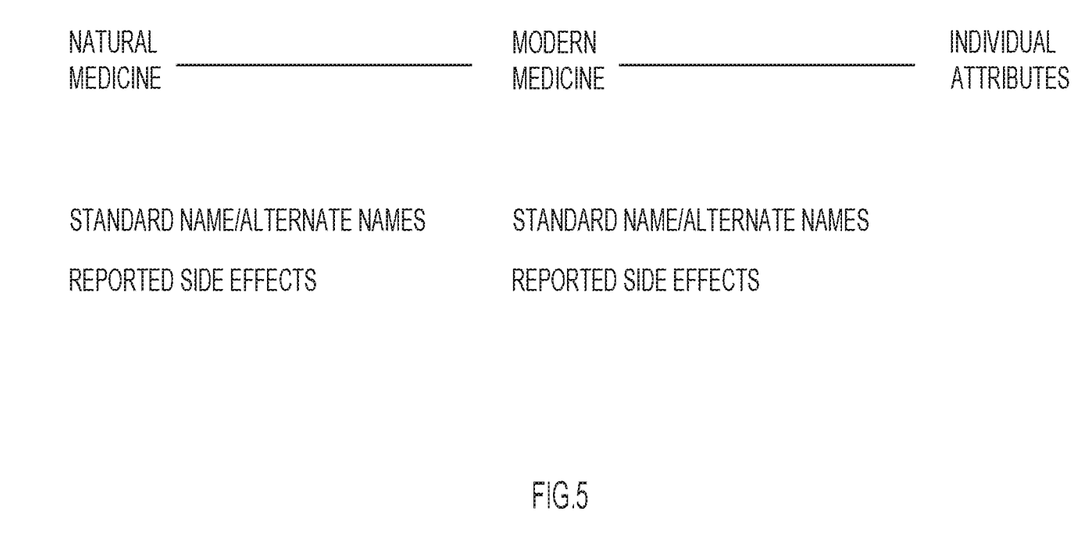
FIG. 5 is a diagram of an ontology showing mapping of natural medicines to modern medicines, according to an embodiment of the present invention.

FIG. 5 shows an example ontology, in which effects for combinations of natural medicines and modern medicines are linked. For example, an individual taking a combination of a natural medicine and a modern medicine may report a specific side effect. The ontology would link the combination of medicines, and would store additional information related to the side effect. In aspects, this information may be further linked to individual attributes/demographics. For example, the ontology may include attributes such as geographic location, age, ethnicity, medical history, medications, etc. This information may be used to construct various online clinical trial groups to study effects of combinations of natural and modern medicines in large groups of individuals over time. This data may be retrospectively analyzed to determine whether individual attributes are linked to observed effects.

Figure 6:
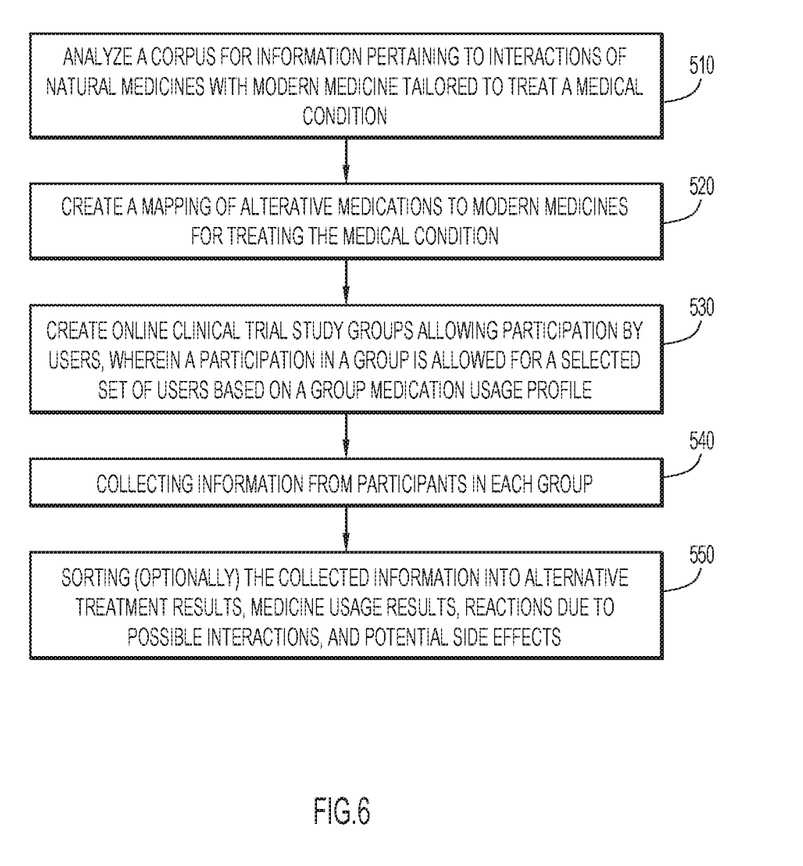
FIG. 6 shows a high level flowchart of operations for implementing a medicinal interaction analysis system, according to an embodiment of the present invention.

FIG. 6 is an operational flow chart showing high level operations of the techniques provided herein. At operation 510, a corpus (e.g., body of works, set of documents, social networking, online forum, etc.) is analyzed for information pertaining to interactions of natural medicines (e.g., including dietary supplements) with modern medicines that treat a medical condition. At operation 520, a mapping operation is performed to create a mapping of alterative medications to modern medicines for treating the condition. At operation 530, online clinical trial study groups G (G1, G2, . . . , GN) are created allowing participation by users U (U1, U2, . . . , UK), wherein a participation in a group GI is allowed for a selected set of users UGI (UGI1, UGI2, . . . , UGIJ) based on a group GI medication usage profile. At operation 540, information is collected from participants in each group GI. At operation 550, the collected information is optionally sorted into alternative treatment results, medicine usage results, reactions due to possible interactions, and potential side effects and reported to relevant parties and/or individuals.

Benefits of the present techniques include uncovering novel natural and modern medicine interactions which may not be known in medical literature. Additionally, present techniques may offer improvements to traditional approaches in designing clinical trials. Traditional approaches may select participants from a random population, or may only consider selection based upon a small number of factors (e.g., a medical characteristic such as presence of a gene or protein, etc.). Such studies may not effectively be designed to uncover effects in specific populations of people. Present techniques offer the ability to design clinical trials with groups of individuals taking a specific combination of medicines with specific population characteristics. Effects may appear in the clinical trial study groups, and therefore, may require fewer clinical trials and less effort to validate in a larger population (e.g., by designing clinical trials with individuals having the same characteristics as the clinical trial study groups).

Present techniques offer an improvement to regulatory aspects of medicines, as potentially unsafe combinations may be identified and further studied for validity. Moreover, these techniques provide a solution in the pharmaceutical sector by using resources specific to the computing industry, namely the ability to establish online clinical trial study groups, using the Internet to obtain information from individuals in any setting having access to the Internet, in a manner that is geographically independent. Unlike modern clinical trials, which are constrained by a particular geography, present techniques offer an improvement of existing approaches, in that data collection is not limited to a localized geographical area. Data may be collected using any device with Internet access. Present techniques allow identification of relevant and/or important medicine interactions, allowing corresponding clinical trials to be designed more efficiently and quickly than existing approaches. More controlled, traditional clinical trials may be conducted as needed, based on this online, mined information.

In further aspects, present techniques may generate online clinical trial study groups in an automated manner. For example, the system may contact a server, and automatically configure access for a set of users. In other aspects, the system may scan online sources to identify users taking a similar combination of medicines, and may automatically send an invitation to join an online clinical trial study groups.

These techniques may be applied to a wide variety of environments, including any environment in which drug interactions may be of concern (e.g., in a medical or clinical setting, in a research or investigational setting, etc.).

It will be appreciated that the embodiments described above and illustrated in the drawings represent only a few of the many ways of implementing embodiments for medicinal interaction analysis.

The environment of the present invention embodiments may include any number of computer or other processing systems (e.g., client or end-user systems, server systems, etc.) and databases or other repositories arranged in any desired fashion, wherein the present invention embodiments may be applied to any desired type of computing environment (e.g., cloud computing, client-server, network computing, mainframe, stand-alone systems, etc.). The computer or other processing system employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, medicinal interaction analysis system 15, etc.). These systems may include any type of monitors and input devices (e.g., keyboard, mouse, voice recognition, etc.) to enter and/or view information.

It is to be understood that the software (e.g., medicinal interaction analysis system 15, including search engine 105, NLP engine 110, mapping engine 115, group generation engine 120, effects engine 125, and aggregator engine 130, etc.) of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments (e.g., medicinal interaction analysis system 15, including search engine 105, NLP engine 110, mapping engine 115, group generation engine 120, effects engine 125, and aggregator engine 130, etc.) may be available on a non-transitory computer useable medium (e.g., magnetic or optical mediums, magneto-optic mediums, floppy diskettes, CD-ROM, DVD, memory devices, SSD, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., extracted data 32, ontology 33, groups 34, and effects 35, etc.). The database system may be implemented by any number of any conventional or other databases, data stores or storage structures (e.g., files, databases, data structures, data or other repositories, etc.) to store information (e.g., extracted data 32, ontology 33, groups 34, and effects 35, etc.). The database system may be included within or coupled to the server and/or client systems. The database systems and/or storage structures may be remote from or local to the computer or other processing systems, and may store any desired data (e.g., extracted data 32, ontology 33, groups 34, and effects 35, etc.).

The present invention embodiments may employ any number of any type of user interface (e.g., Graphical User Interface (GUI), command-line, prompt, etc.) for obtaining or providing information (e.g., information corpus 31, extracted data 32, ontology 33, groups 34, and effects 35, etc.), wherein the interface may include any information arranged in any fashion. The interface may include any number of any types of input or actuation mechanisms (e.g., buttons, icons, fields, boxes, links, etc.) disposed at any location to enter/display information and initiate desired actions via any suitable input devices (e.g., mouse, keyboard, voice, etc.). The interface screens may include any suitable actuators (e.g., links, tabs, etc.) to navigate between the screens in any fashion.

The output of the medicinal interaction analysis system 15 may include any information arranged in any fashion, and may be configurable based on rules or other criteria to provide desired information to a user (e.g., interactions, rankings, ontologies, clinical trial study groups, etc.).

The present invention embodiments are not limited to the specific tasks or algorithms described above, but may be utilized for any application in which identifying medicine interactions may be desirable in a general population. Further, this approach may be generally applicable to providing support in any context, and is not limited to any particular application domain, such as clinical, investigation, biomedical, research-oriented, etc.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state disk (SSD), a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be accomplished as one step, executed concurrently, substantially concurrently, in a partially or wholly temporally overlapping manner, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for monitoring usage of a medicine comprising:
    analyzing, via a processor, a corpus by natural language processing to extract information pertaining to interactions of natural medicines with modern medicines tailored to treat a medical condition, wherein the natural medicines include homeopathic and herbal remedies and the modern medicines include synthetic medicines;
    identifying, via the processor, a combination of three or more of the natural medicines and modern medicines associated with side effects of a user, wherein the identifying includes:
        determining that at least one of the natural medicines has an unknown ingredient;
        determining a plant from which the at least one natural medicine having the unknown ingredient is derived; and
        identifying the combination based on the side effects of the determined plant;
    determining by natural language processing of the corpus, via the processor, different sets of medicines derived from the combination, wherein the sets of medicines are associated with other users and include at least one set including the combination and one or more other natural or modern medicines and at least one set including a sub-combination of the combination;
    analyzing, via the processor, the determined sets of medicines from the corpus to identify sets of medicines having side effects corresponding to the combination and to determine sets of medicines without side effects;
    creating, via the processor, a mapping of the natural medicines to the modern medicines for treating the medical condition based on the combination and the identified sets of medicines, wherein creating the mapping comprises:
        generating an ontology comprising natural medicines, modern medicines, and user demographics; and
        anonymizing user identity and user medical characteristics of the ontology to allow data of the ontology to be analyzed without identifying user identities pertaining to the data;
    creating, via the processor, online clinical trial study groups of participants for a clinical trial by analyzing the data of the ontology to identify attributes of users reporting side effects without identifying corresponding user identities, wherein participation in an online clinical trial study group is allowed for a selected set of participants having attributes of users of one of the combination and an identified set of medicines;
    validating the side effects of the combination and the identified sets of medicines by conducting the clinical trial online, via the processor, and collecting information from participants in each online clinical trial study group; and
    reporting, via the processor, results of the collected information.

2. The method of claim 1, further comprising:
    providing a summary of the collected information, wherein side effects are ranked by frequency.

3. The method of claim 1, further comprising:
    establishing the online clinical trial study groups in an online forum in an automated manner.

4. The method of claim 1, wherein the corpus includes an online forum, a private database, a public database and/or a social media forum.

5. The method of claim 1, wherein the collected information includes adverse effects, beneficial effects, medicine profiles of the participants, and demographic information of the participants.

6. The method of claim 1, further comprising determining whether an effect between a modern medicine and a natural medicine is statistically significant among the participants in an online clinical trial study group.

7. The method of claim 1, further comprising:
    determining which combinations of natural medicine and modern medicine of a plurality of medicines consumed by users are statistically correlated with an effect.

8. A computer system for monitoring usage of a medicine, the computer system comprising:
    one or more computer processors;
    one or more computer readable storage media;
    program instructions stored on the one or more computer readable storage media for execution by at least one of the one or more computer processors, the program instructions comprising instructions to:
        analyze a corpus by natural language processing to extract information pertaining to interactions of natural medicines with modern medicines tailored to treat a medical condition, wherein the natural medicines include homeopathic and herbal remedies and the modern medicines include synthetic medicines;
        identify a combination of three or more of the natural medicines and modern medicines associated with side effects of a user, wherein the identifying includes:
            determining that at least one of the natural medicines has an unknown ingredient;
            determining a plant from which the at least one natural medicine having the unknown ingredient is derived; and
            identifying the combination based on the side effects of the determined plant;
        determine by natural language processing of the corpus different sets of medicines derived from the combination, wherein the sets of medicines are associated with other users and include at least one set including the combination and one or more other natural or modern medicines and at least one set including a sub-combination of the combination;

analyze the determined sets of medicines from the corpus to identify sets of medicines having side effects corresponding to the combination and to determine sets of medicines without side effects;

create a mapping of the natural medicines to the modern medicines for treating the medical condition based on the combination and the identified sets of medicines, wherein creating the mapping comprises:
generating an ontology comprising natural medicines, modern medicines, and user demographics; and
anonymizing user identity and user medical characteristics of the ontology to allow data of the ontology to be analyzed without identifying user identities pertaining to the data;

create online clinical trial study groups of participants for a clinical trial by analyzing the data of the ontology to identify attributes of users reporting side effects without identifying corresponding user identities, wherein participation in an online clinical trial study group is allowed for a selected set of participants having attributes of users of one of the combination and an identified set of medicines;

validate the side effects of the combination and the identified sets of medicines by conducting the clinical trial online and collecting information from participants in each online clinical trial study group; and report results of the collected information.

9. The computer system of claim 8, wherein the program instructions further comprise instructions to provide a summary of the collected information, wherein side effects are ranked by frequency.

10. The computer system of claim 8, wherein the program instructions further comprise instructions to establish the online clinical trial study groups in an online forum in an automated manner.

11. The computer system of claim 8, wherein the program instructions further comprise instructions to determine whether an effect between a modern medicine and a natural medicine is statistically significant among the participants in an online clinical trial study group.

12. The computer system of claim 8, wherein the program instructions further comprise instructions to determine which combinations of natural medicine and modern medicine of a plurality of medicines consumed by users are statistically correlated with an effect.

13. A computer program product for monitoring usage of a medicine, the computer program product comprising one or more computer readable storage media collectively having program instructions embodied therewith, the program instructions executable by a computer to cause the computer to:

analyze a corpus by natural language processing to extract information pertaining to interactions of natural medicines with modern medicines tailored to treat a medical condition, wherein the natural medicines include homeopathic and herbal remedies and the modern medicines include synthetic medicines;

identify a combination of three or more of the natural medicines and modern medicines associated with side effects of a user, wherein the identifying includes:
determining that at least one of the natural medicines has an unknown ingredient;
determining a plant from which the at least one natural medicine having the unknown ingredient is derived; and
identifying the combination based on the side effects of the determined plant;

determine by natural language processing of the corpus different sets of medicines derived from the combination, wherein the sets of medicines are associated with other users and include at least one set including the combination and one or more other natural or modern medicines and at least one set including a sub-combination of the combination;

analyze the determined sets of medicines from the corpus to identify sets of medicines having side effects corresponding to the combination and to determine sets of medicines without side effects;

create a mapping of the natural medicines to the modern medicines for treating the medical condition based on the combination and the identified sets of medicines, wherein creating the mapping comprises:
generating an ontology comprising natural medicines, modern medicines, and user demographics; and
anonymizing user identity and user medical characteristics of the ontology to allow data of the ontology to be analyzed without identifying user identities pertaining to the data;

create online clinical trial study groups of participants for a clinical trial by analyzing the data of the ontology to identify attributes of users reporting side effects without identifying corresponding user identities, wherein participation in an online clinical trial study group is allowed for a selected set of participants having attributes of users of one of the combination and an identified set of medicines;

validate the side effects of the combination and the identified sets of medicines by conducting the clinical trial online and collecting information from participants in each online clinical trial study group; and report results of the collected information.

14. The computer program product of claim 13, wherein the program instructions further cause the computer to provide a summary of the collected information, wherein side effects are ranked by frequency.

15. The computer program product of claim 13, wherein the program instructions further cause the computer to determine whether an effect between a modern medicine and a natural medicine is statistically significant among the participants in an online clinical trial study group.

16. The computer program product of claim 13, wherein the program instructions further cause the computer to determine which combinations of natural medicine and modern medicine of a plurality of medicines consumed by users are statistically correlated with an effect.

* * * * *